Figure 1:
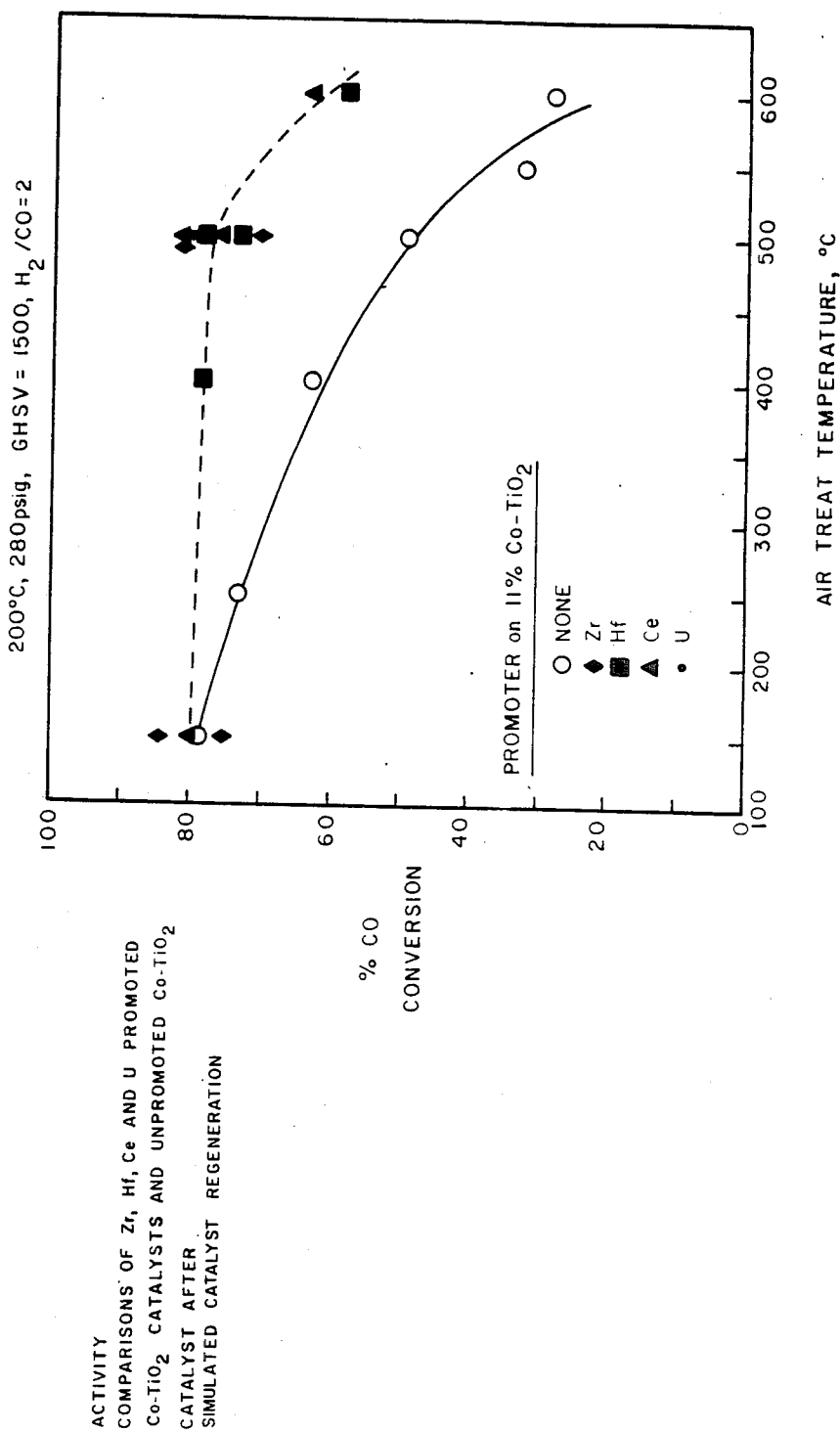

United States Patent [19]

Mauldin et al.

[11] Patent Number: 4,762,959

[45] Date of Patent: Aug. 9, 1988

[54] COBALT CATALYSTS, AND USE THEREOF FOR THE CONVERSION OF METHANOL AND FOR FISCHER-TROPSCH SYNTHESIS, TO PRODUCE HYDROCARBONS

[75] Inventors: Charles H. Mauldin; Stephen M. Davis; Kym B. Arcuri, all of Baton Rouge, La.

[73] Assignee: Exxon Research and Engineering Company, Florham Park, N.J.

[21] Appl. No.: 57,302

[22] Filed: Jun. 4, 1987

Related U.S. Application Data

[62] Division of Ser. No. 922,885, Oct. 24, 1986, which is a division of Ser. No. 813,918, Dec. 27, 1985, Pat. No. 4,663,305.

[51] Int. Cl.$^4$ .............................................. C07C 1/00
[52] U.S. Cl. ..................................... 585/640; 585/733
[58] Field of Search ................................ 585/640, 733

Primary Examiner—Curtis R. Davis
Attorney, Agent, or Firm—Roy J. Ott

[57] ABSTRACT

A zirconium, hafnium, cerium or uranium promoted cobalt catalyst and process for the conversion of methanol or synthesis gas to hydrocarbons. Methanol is contacted, preferably with added hydrogen, over said catalyst, or synthesis gas is contacted over said catalyst to produce, at reaction conditions, an admixture of $C_{10+}$ linear paraffins and olefins. These hydrocarbons can be further refined to high quality middle distillate fuels, and other valuable products such as mogas, diesel fuel, and jet fuel, particularly premium middle distillate fuels of carbon number ranging to about $C_{20}$.

6 Claims, 2 Drawing Sheets

ACTIVITY
COMPARISONS OF Zr, Hf, Ce AND U PROMOTED
Co-TiO₂ CATALYSTS AND UNPROMOTED Co-TiO₂
CATALYST AFTER
SIMULATED CATALYST REGENERATION

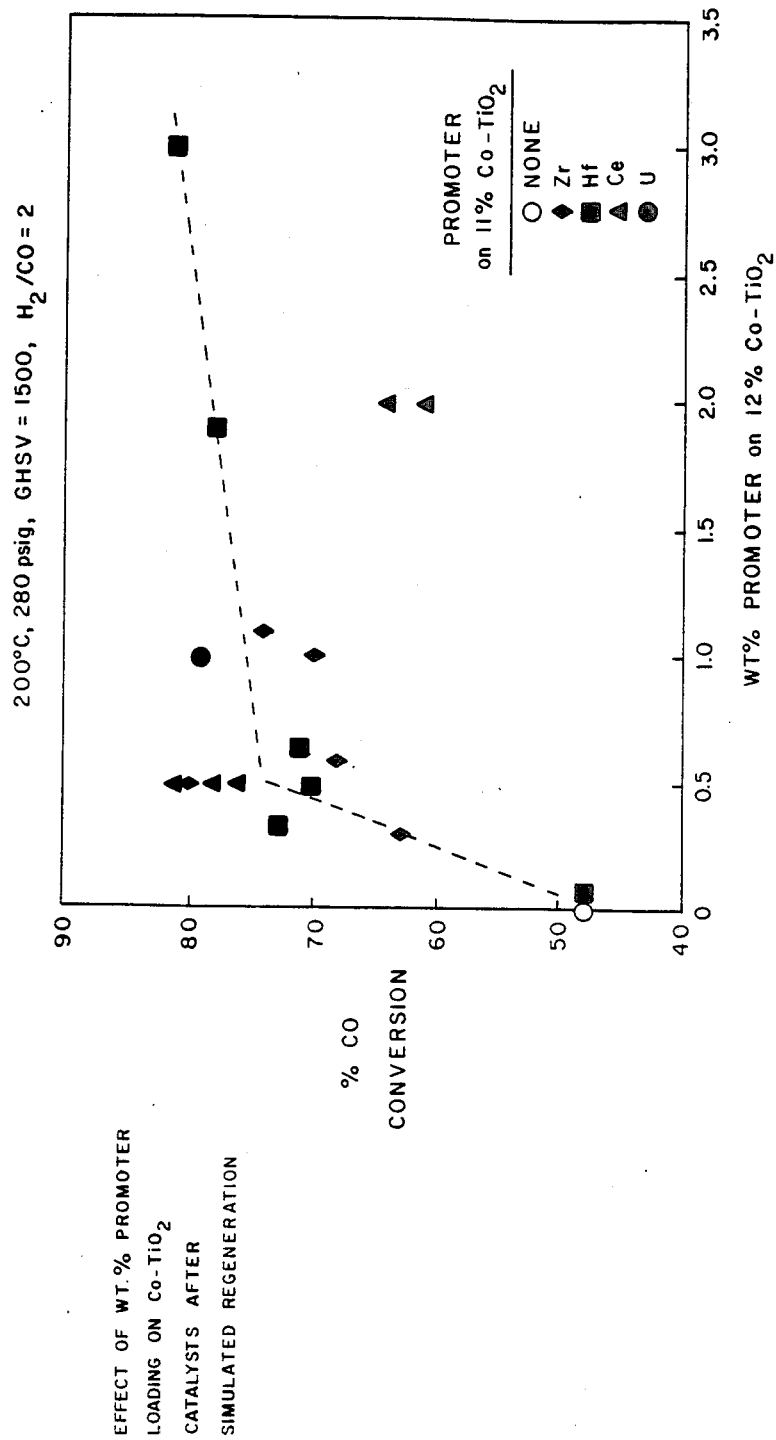

COBALT CATALYSTS, AND USE THEREOF FOR THE CONVERSION OF METHANOL AND FOR FISCHER-TROPSCH SYNTHESIS, TO PRODUCE HYDROCARBONS

This is a division of application Ser. No. 922,885, filed Oct. 24, 1986, which is a division of application Ser. No. 813,918 filed Dec. 27, 1985, now U.S. Pat. No. 4,663,305.

BACKGROUND OF THE INVENTION

I. Field of the Invention

This invention relates to improvements in a process for the conversion of methanol to hydrocarbons, to improvements in a Fischer-Tropsch process for the production of hydrocarbons, and to improvements made in catalysts employed to conduct such processes. In particular, it relates to improved cobalt catalysts, and process for using such catalysts in the conversion of methanol, and Fischer-Tropsch synthesis to produce hydrocarbons, especially $C_{10}+$ distillate fuels, and other valuable products.

II. Background

A need exists for the creation, development, and improvement of catalysts and processes, useful for the conversion of methanol and synthesis gases to hydrocarbons, especially high quality transportation fuels. Methane is available in large quantities, either as an undesirable by-product or off-gas from process units, or from oil and gas fields. The existence of large methane, natural gas reserves coupled with the need to produce premium grade transportation fuels, particularly middle distillate fuels, thus poses a major incentive for the development of new gas-to-liquids processes. However, whereas technology is available for the conversion of natural gas to methanol, in order to utilize this technology there is a need for new or improved catalysts, and processes suitable for the conversion of methanol to high quality transportation fuels, particularly middle distillate fuels.

The technology needed to convert natural gas, or methane, to synthesis gas is also well established. It is also known that synthesis gas can be converted to hydrocarbons via Fischer-Tropsch synthesis, though new or improved catalysts, and processes for carrying out Fischer-Tropsch reactions are much needed. Fischer-Tropsch synthesis for the production of hydrocarbons from carbon monoxide and hydrogen is well known in the technical and patent literature. Commercial units have also been operated, or are being operated in some parts of the world. The first commercial Fischer-Tropsch operation utilized a cobalt catalyst, though later more active iron catalysts were also commercialized. An important advance in Fischer-Tropsch catalysts occurred with the use of nickel-thoria on Kieselguhr in the early thirties. This catalyst was followed within a year by the corresponding cobalt catalyst, 100 Co:18 ThO$_2$:100 Kieselguhr, parts by weight, and over the next few years by catalysts constituted to 100 Co:18 ThO$_2$:200 Kieselguhr and 100 Co:5 ThO$_2$:8 MgO:200 Kieselguhr, respectively. The Group VIII non-noble metals, i.e., iron, cobalt, and nickel, have been widely used in Fischer-Tropsch reactions, and these metals have been promoted with various other metals, and supported in various ways on various substrates. Most commercial experience has been based on cobalt and iron catalysts. The cobalt catalysts, however, are of generally low activity necessitating a multiple staged process, as well as low synthesis gas throughput. The iron catalysts, on the other hand, are not really suitable for natural gas conversion due to the high degree of water gas shift activity possessed by iron catalysts. Thus, more of the synthesis gas is converted to carbon dioxide in accordance with the equation: $H_2 + 2CO \rightarrow (CH_2)_x + CO_2$; with too little of the synthesis gas being converted to hydrocarbons and water as in the more desirable reaction, represented by the equation: $2H_2 + CO \rightarrow (CH_2)_x + H_2O$.

The need for a catalyst composition, and process useful for the conversion of methanol or synthesis gas at high conversion levels, and at high yields to premium grade transportation fuels, particularly without the production of excessive amounts of carbon dioxide, were met in large part by the novel catalyst compositions, and processes described in U.S. application Ser. Nos. 626,013; 626,023; and 626,026, filed June 29, 1984, by Payne and Mauldin; now U.S. Pat. Nos. 4,542,122, 4,595,703, and 4,556,752. The preferred catalysts therein described are characterized as particulate catalyst compositions constituted of a titania or titania-containing support, preferably a titania support having a rutile:anatase content of at least about 2:3, upon which there is dispersed a catalytically active amount of cobalt, or cobalt and thoria. These catalyst compositions possess good activity and stability and can be employed over long periods to produce hydrocarbons from methanol, or to synthesize hydrocarbons from carbon monoxide and hydrogen.

These cobalt-titania catalysts it was found, like most hydrocarbon synthesis catalysts, became coated during an "on-oil" run with a carbonaceous residue, i.e., coke, formed either during extended periods of operation or during feed or temperature upsets. The initially high activity of the catalysts declines during the operation due to the coke deposits thereon, and the operating temperature must be increased to maintain an acceptable level of conversion. Eventually the catalysts become deactivated to a point where the temperature required to maintain an acceptable conversion level causes excessive formation of methane and other light hydrocarbon gases at the expense of the desired $C_{10}+$ hydrocarbons, at which point it becomes necessary to regenerate, and reactivate the catalyst. Unlike many other catalysts commonly used by the refining industry however, when the coke deposits were burned from the cobalt-titania catalysts at oxidizing conditions by contact with air (or oxygen) at elevated temperatures, and the catalysts thereafter treated with hydrogen to reduce the cobalt metal component, the initially high activity of the cobalt-titania catalysts did not return to that of a fresh catalyst. Rather, their activity was considerably less than that of fresh cobalt-titania catalysts. Moreover, after the regeneration, and reactivation of the catalysts, there was no improvement in the rate of deactivation and the deactivation proceeded from a lower initial activity. This loss in the overall activity brought about by burning the coke from these catalysts at elevated temperatures in the presence of air (oxygen) is not only detrimental per se, but severely restricts the overall life of the catalyst, and threatens their full utilization in commercial operations.

III. Objects

It is, accordingly, a primary objective of the present invention to obviate this problem.

In particular, it is an object to provide novel and improved cobalt-titania catalysts, and processes utilizing such catalysts, for the conversion of methanol or synthesis gas to high quality transportation fuels, especially distillate fuels characterized generally as admixtures of $C_{10}+$ linear paraffins and olefins.

A more specific object is to provide new and improved supported cobalt-titania catalysts, which in methanol conversion and Fischer-Tropsch synthesis reactions are not only highly active and stable prior to regeneration, and reactivation, but capable after regeneration, and reactivation, of recovering their initial high activity, while maintaining their stability.

A further object is to provide a process which utilizes such catalysts for the preparation of hydrocarbons, notably high quality middle distillate fuels characterized generally as admixtures of linear paraffins and olefins, from methanol, or from a feed mixture of carbon monoxide and hydrogen via the use of such catalysts.

IV. The Invention

These objects and others are achieved in accordance with the present invention which, in general, embodies:

(A) A particulate catalyst composition constituted of titania, or a titania-containing support, on which there is dispersed a catalytically active amount of cobalt sufficient to provide good activity and stability in the production of hydrocarbons from methanol, or in the production of hydrocarbons via carbon monoxide-hydrogen synthesis reactions, and sufficient of a metal promoter selected from the group consisting of zirconium, hafnium [i.e., Group IVB metals of the Periodic Table of the Elements (E. H. Sargent & Co., Copyright 1962, Dyna-Slide Co.) having an atomic weight greater than 90] cerium (a lanthanium series metal), and uranium (an actinium series metal), or admixture of these metals with each other or with other metals, such that after oxidizing the cobalt at elevated temperature, as occurs after the deposition of coke thereon during an operating run, the catalyst can be regeneratedr by burning the coke therefrom by contact at elevated temperature with oxygen or an oxygen-containing gas (e.g., air), and then reactivated by contact of the catalyst with a reducing gas, particularly hydrogen, to reduce the cobalt metal component such that the activity and stability of the catalyst is thereby restored. Suitably, in terms of absolute concentrations the cobalt is present in amounts ranging from about 2 percent to about 25 percent, preferably from about 5 percent to about 15 percent, calculated as metallic metal based on the total weight of the catalyst composition (dry basis). The zirconium, hafnium, cerium, or uranium in the form of a salt or compound of said promoter metal, is added to the cobalt-titania catalyst, in amount sufficient to form a catalyst composite the activity and stability of which after regeneration, and reactivation, approximates that of a fresh cobalt-titania catalyst, i.e., a catalyst, cobalt-titania catalyst which has never been regenerated. The promoter metal is quite effective in low concentrations, concentrations greater than that required to provide the desired regenerability generally offering little, or no further benefit. The efficiency of the promoter metals is believed generally related to their highly dispersed physical state over the surface of the titania support. Suitably, a cobalt-titania catalyst can be made regenerable by compositing therewith a zirconium, hafnium, cerium, or uranium metal in weight ratio of metal:cobalt greater than about 0.010:1, preferably from about 0.025:1 to about 0.10:1. One of more of said promoter metals—viz., zirconium, hafnium, cerium, or uranium—is dispersed with the catalytically active amount of cobalt upon a titania support, particularly a titania support wherein the rutile:anatase weight ratio is at least about 2:3. The rutile:anatase ratio is determined in accordance with ASTM D 3720-78: Standard Test Method for *Ratio of Anatase to Rutile in Titanium Dioxide Pigments By Use of X-Ray Diffraction.* The absolute concentration of the cobalt and promoter metal is preselected to provide the desired ratio of the zirconium, hafnium, cerium, or uranium metal:cobalt. Zirconium is a preferred Group IVB metal in terms of its cost-effectiveness, and a cobalt-titania catalyst to which zirconium is added in weight ratio of zirconia:cobalt greater than 0.010:1, preferably from about 0.04:1 to about 0.25:1 has been found to form a catalyst which is highly regeneration stable. This catalyst has been found capable of continued sequences of regeneration with essentially complete recovery of its initial activity when the catalyst is returned to an on-oil operation, and there is no loss in stability in either methanol conversion or hydrocarbon synthesis reactions. The cobalt-titania catalyst compositions when stabilized with any one, or admixture of zirconium, hafnium, cerium, or uranium, it has been found, produce a product which is predominately $C_{10}+$ linear paraffins and olefins, with very little oxygenates. These promoted catalyst species provide essentially the same high selectivity, high activity, and high activity maintenance after regeneration in methanol conversion, or in the conversion of the carbon monoxide and hydrogen to distillate fuels, as freshly prepared unpromoted cobalt-titania catalysts (i.e., catalysts otherwise similar except that no zirconium, hafnium, cerium or uranium have been composited therewith) which have never been regenerated, or subjected to regeneration conditions. The promoted cobalt-titania catalysts are thus highly regeneration stable, the activity and stability of the promoted catalyst being restored after regeneration to that of an unpromoted cobalt-titania catalyst which has never been regenerated by burning off the coke at high temperature in air under oxidizing conditions.

(B) A process wherein the particulate zirconium, hafnium, cerium, or uranium promoted cobalt-titania catalyst composition of (A), supra, is formed into a bed, and the bed of catalyst contacted at reaction conditions with a methanol feed, or feed comprised of an admixture of carbon monoxide and hydrogen, or compound decomposable in situ within the bed to generate carbon monoxide and hydrogen, to produce a middle distillate fuel product constituted predominately of linear paraffins and olefins, particularly $C_{10}+$ linear paraffins and olefins.

(i) In conducting the methanol reaction the partial pressure of methanol within the reaction mixture is generally maintained above about 100 pounds per square inch absolute (psia), and preferably above about 200 psia. It is often preferable to add hydrogen with the methanol. Suitably, methanol and hydrogen are employed in molar ratio of $CH_3OH:H_2$ above about 4:1, and preferably above 8:1, to increase the concentration of $C_{10}+$ hydrocarbons in the product. Suitably, the $CH_3OH:H_2$ molar ratio, where hydrogen is employed, ranges from about 4:1 to about 60:1, and preferably the methanol and hydrogen are employed in molar ratio ranging from about 8:1 to about 30:1. Inlet hydrogen partial pressures preferably range below about 80 psia, and more preferably below about 40 psia; inlet hydrogen partial pressures preferably ranging from about 5 psia to about 80 psia, and more preferably from about 10 psia to about 40 psia. In general, the reaction is carried out at liquid hourly space velocities ranging from about 0.1 hr$^{-1}$ to about 10 hr$^{-1}$, preferably from about 0.2 hr$^{-1}$ to about 2 hr$^{-1}$, and at temperatures ranging from about 150° C. to about 350° C., preferably from about 180° C. to about 250° C. Methanol partial pressures preferably range from about 100 psia to about 1000 psia, more preferably from about 200 psia to about 700 psia.

(ii) The synthesis reaction is generally carried out at an H$_2$:CO mole ratio of greater than about 0.5, and preferably the H$_2$:CO mole ratio ranges from about 0.1 to about 10, more preferably from about 0.5 to about 4, at gas hourly space velocities ranging from about 100 V/Hr/V to about 5000 V/Hr/V, preferably from about 300 V/Hr/V to about 1500 V/Hr/V, at temperatures ranging from about 160° C. to about 290° C., preferably from about 190° C. to about 260° C., and pressures above about 80 psig, preferably ranging from about 80 psig to about 600 psig, more preferably from about 140 psig to about 400 psig.

The product of either the methanol conversion reaction, or synthesis reaction generally and preferably contains 45 percent or greater, more preferably 60 percent or greater, C$_{10}$+liquid hydrocarbons which boil above 160° C. (320° F.).

In forming the catalyst, titania is used as a support, or in combination with other materials for forming a support. The titania used for the support in either methanol or syngas conversions, however, is preferably one where the rutile:anatase ratio is at least about 2:3 as determined by x-ray diffraction (ASTM D 3720-78). Preferably, the titania used for the catalyst support of catalysts used in syngas conversion is one wherein the rutile:anatase ratio is at least about 3:2. Suitably the titania used for syngas conversions is one containing a rutile:anatase ratio of form about 3:2 to about 100:1, or higher, preferably from about 4:1 to about 100:1, or higher. A preferred, and more selective catalyst for use in methanol conversion reactions is one containing titania wherein the rutile:anatase ranges from about 2:3 to about 3:2. The surface area of such forms of titania are less than about 50 m$^2$/g. This weight of rutile provides generally optimum activity, and C$_{10}$+hydrocarbon selectivity without significant gas and CO$_2$ make.

The zirconium, hafnium, cerium, or uranium promoted cobalt-titania catalyst prior to regeneration, it was found, will have essentially the same high activity as the corresponding unpromoted cobalt-titania catalyst. Thus, during an initial, on-oil operating run, or run wherein hydrocarbons are being produced over the fresh catalyst by methanol conversion or hydrocarbon synthesis from carbon monoxide and hydrogen the activity of the two different catalysts is not essentially different. Unlike an unpromoted cobalt-titania catalyst, or catalyst otherwise similar except that it does not contain zirconium, hafnium, cerium, or uranium, however, the initial high activity of the promoted cobalt-titania catalyst will be maintained even after regeneration of the coked catalyst which is accomplished by burning off the coke deposits at elevated temperature in an oxygen-containing gas (e.g., air), and the catalyst then reduced, as by contact of the catalyst with hydrogen, or a hydrogen-containing gas. Moreover, the stability of the promoted cobalt-catalyst will be maintained, this catalyst deactivating in an on-oil run at corresponding conditions at no greater rate than that of any unpromoted cobalt-titania catalyst, or catalyst otherwise similar except that it does not contain zirconium, hafnium, cerium, or uranium, which has never been regenerated. Whereas the unpromoted, fresh cobalt-titania catalyst was thus found to possess an initial high activity in an on-oil operation, it was subsequently found that the activity of this catalyst was not completely restored after regeneration, the catalyst recovering only about 50 percent of the activity formerly possessed by the fresh catalyst. Moreover, after initiation of an on-oil operation, the activity of the regenerated zirconium, hafnium, cerium, or uranium promoted cobalt-titania will decline at about the same rate as that of the fresh unpromoted cobalt-titania catalyst. Retention of this activity and stability by the promoted cobalt-titania catalysts thus effectively eliminates the disadvantages formerly associated with unpromoted cobalt-titania catalysts, and makes possible full utilization of cobalt-titania catalysts in commercial operations.

Cobalt-titania catalysts, like most hydrocarbon synthesis catalysts are primarily deactivated during on-oil operation by the deposition thereon of a carbonaceous residue, i.e., coke, formed either during extended periods of operation or during feed or temperature upsets. It was thought that the coked catalyst could be regenerated and its initial activity restored by burning the coke from the catalyst. Air burns at, e.g., 400°–500° C., are thus normally effective in removing essentially all of the carbon from a catalyst, this offering a relatively simple, commercially feasible technique for regenerating deactivated cobalt-titania catalysts. However, in order for air regeneration to restore activity, the catalytic cobalt metal must be maintained in dispersed state at both on-oil and regeneration conditions. Albeit the unpromoted cobalt catalyst upon which the cobalt was well dispersed was found to be stable during an on-oil operation, the cobalt agglomerated during high temperature air treatment. It is found however, that even in low concentration, zirconium, hafnium, cerium, or uranium, or admixture thereof, could be used as an additive to stabilize the cobalt-titania catalyst not only by maintaining the cobalt in a dispersed state upon the titania during on-oil operations, but also during air burns, thus providing a readily regenerable catalyst.

Whereas Applicants do not wish to be bound by any specific mechanistic theory, it is believed that the action of the zirconium, hafnium, cerium, or uranium metals in promoting the regenerability of a cobalt-titania catalyst during an air burn can be explained, at least in part. Thus, during an air burn the crystallites of metallic cobalt of a cobalt-titania catalyst are oxidized to form Co$_3$O$_4$ which agglomerates at temperatures above about 350° C. After reactivation of the catalyst by contact with hydrogen cobalt metal agglomerates are formed which are of larger crystallite size than the original metallic crystallites of cobalt metal. Large agglomerates of cobalt form catalysts which are less active than catalysts formed with more finely dispersed cobalt. The zirconium, hafnium, cerium, or uranium promoter metals of the promoted cobalt-titania catalyst are present as highly dispersed oxides over the TiO$_2$ support surface, and all are of a cubic crystal structure (except for Ce which can exist either as cubic CeO$_2$, or hexagonal Ce$_2$O$_3$). These oxides are believed to form a strong surface interaction with Co$_3$O$_4$ which is also of cubic crystal structure. The cubic oxide promoters are thus believed to form a matrix, or act as a "glue" between the Co$_3$O$_4$ and TiO$_2$, and maintain the cobalt in finely dispersed form upon the support surface.

The catalysts of this invention may be prepared by techniques known in the art for the preparation of other catalysts. The catalyst can, e.g., be prepared by gellation, or cogellation techniques. Suitably, however, the cobalt, zirconium, hafnium, cerium, or uranium metals, or admixtures of these metals with each other, or with other metals, can be deposited on a previously pilled, pelleted, beaded, extruded, or sieved support material by the impregnation method. In preparing catalysts, the metals are deposited from solution on the support in preselected amounts to provide the desired absolute amounts, and weight ratio of the respective metals, e.g., cobalt and zirconium or hafnium, or cobalt and an admixture of zirconium and hafnium. Suitably, the cobalt and zirconium, hafnium, cerium, or uranium metals are composited with the support by contacting the support with a solution of a cobalt-containing compound, or salt, e.g., cobalt nitrate, acetate, acetylacetonate, napthenate, carbonyl, or the like, and a promoter metal-containing compound, or salt. One metal can be composited with the support, and then the other. For example, the promoter metal can first be impregnated upon the support, followed by impregnation of the cobalt, or vice versa. Optionally, the promoter metal and cobalt can be coimpregnated upon the support. The cobalt and promoter metal compounds used in the impregnation can be any organometallic or inorganic compounds which will decompose to give cobalt, and zirconium, hafnium, cerium, or uranium oxides upon calcination, e.g., a cobalt, zirconium, or hafnium nitrate, acetate, acetylacetonate, naphthenate, carbonyl, or the like. The amount of impregnation solution used should be sufficient to completely immerse the carrier, usually within the range from about 1 to 20 times of the carrier by volume, depending on the metal, or metals, concentration in the impregnation solution. The impregnation treatment can be carried out under a wide range of conditions including ambient or elevated temperatures. Metal components other than cobalt and a promoter metal, or metals, can also be added. The introduction of an additional metal, or metals, into the catalyst can be carried out by any method and at any time of the catalyst preparation, for example, prior to, following, or simultaneously with the impregnation of the support with the cobalt and zirconium, hafnium, cerium, or uranium metal components. In the usual operation, the additional component is introduced simultaneously with the incorporation of the cobalt and the zirconium, and hafnium, cerium, or uranium components.

It is preferred to first impregnate the zirconium, hafnium, cerium, or uranium metal, or metals onto the support, or to coimpregnate the zirconium, hafnium, cerium, or uranium metal, or metal with the cobalt into the titania support, and then to dry and calcine the catalyst. Thus, in one technique for preparing a catalyst a titania, or titania-containing support, is first impregnated with the zirconium, hafnium, cerium, or uranium metal salt, or compound, and then dried or calcined at conventional conditions. Cobalt is then dispersed on the precalcined support on which the zirconium, hafnium, cerium, or uranium metal, or metals, has been dispersed and the catalyst again dried, and calcined. Or, the zirconium, hafnium, cerium, or uranium metal, or metals, may be coimpregnated onto the support, and the catalyst then dried, and calcined. The zirconium, hafnium, cerium and uranium metals are believed to exist in the finished freshly calcined catalyst as an oxide, the metal oxides being more closely associated with the titania support than with the cobalt.

The promoted cobalt-titania catalyst, after impregnation of the support, is dried by heating at a temperature above about 30° C., preferably between 30° C. and 125° C., in the presence of nitrogen or oxygen, or both, or air, in a gas stream or under vacuum. It is necessary to activate the finished catalyst prior to use. Preferably, the catalyst is contacted in a first step with oxygen, air, or other oxygen-containing gas at temperature sufficient to oxidize the cobalt, and convert the cobalt to Co$_3$O$_4$. Temperatures ranging above about 150° C., and preferably above about 200° C., are satisfactory to convert the cobalt to the oxide, but temperatures up to about 500° C., such as might be used in the regeneration of a severely deactivated catalyst, can be tolerated. Suitably, the oxidation of the cobalt is achieved at temperatures ranging from about 150° C. to about 300° C. The cobalt oxide contained on the catalyst is then reduced to cobalt metal to activate the catalyst. Reduction is performed by contact of the catalyst, whether or not previously oxidized, with a reducing gas, suitably with hydrogen or a hydrogen-containing gas stream at temperatures above about 250° C.; preferably above about 300° C. Suitably, the catalyst is reduced at temperatures ranging from about 250° C. to about 500° C., and preferably from about 300° C. to about 450° C., for periods ranging from about 0.5 to about 24 hours at pressures ranging from ambient to about 40 atmospheres. Hydrogen, or a gas containing hydrogen and inert components in admixture is satisfactory for use in carrying out the reduction.

In the regeneration step, the coke is burned from the catalyst. The catalyst can be contacted with a dilute oxygen-containing gas and the coke burned from the catalyst at controlled temperature below the sintering temperature of the catalyst. The temperature of the burn is maintained at the desired level by controlling the oxygen concentration and inlet gas temperature, this taking into consideration the amount of coke to be removed and the time desired to complete the burn. Generally, the catalyst is treated with a gas having an oxygen partial pressure above about 0.1 pounds per square inch (psi), and preferably in the range of from about 0.3 psi to about 2.0 psi, to provide a temperature ranging from about 300° C. to about 550° C., at static or dynamic conditions, preferably the latter, for a time sufficient to remove the coke deposits. Coke burn-off can be accomplished by first introducing only enough oxygen to initiate the burn while maintaining a temperature on the low side of this range, and gradually increasing the temperature as the flame front is advanced by additional oxygen injection until the temperature has reached optimum. Most of the coke can generally be removed in this way. The catalyst is then reactivated by treatment with hydrogen or hydrogen-containing gas as with a fresh catalyst.

The invention will be more fully understood by reference to the following demonstrations and examples which present comparative data illustrating its more salient features. All parts are given in terms of weight except as otherwise specified. Feed compositions are expressed as molar ratios of the components.

The addition of a small amount of hafnium, zirconium, cerium, or uranium, respectively, to a Co-TiO$_2$ catalyst maintains the cobalt in a high state of dispersion and stabilizes the catalyst during high temperature air treatments. The added zirconium, hafnium, cerium, or uranium metal thus maintains during and after regeneration the very high intrinsic activity of the catalyst which is characteristic of a fresh catalyst having well-dispersed cobalt on the TiO$_2$. The high intrinsic activity of the promoted Co-TiO$_2$ permits, after regeneration, the same high conversion operations at low temperature, where excellent selectivity is obtained in the conversion of methanol or syngas to C$_{10}$+hydrocarbons as with a fresh catalyst.

In the following example, the results of a series of runs are given wherein various metals, inclusive of zirconium, hafnium, cerium, and uranium, respectively, were added to portions of a freshly prepared Co-TiO$_2$ catalyst, these specimens of catalyst being compared with a portion of the Co-TiO$_2$ catalyst to which no promoter metal was added. These catalysts were calcined by contact with air at elevated temperature in a simulated coke burn, activated by contact with hydrogen, and then employed in a Fischer-Tropsch reaction. The metal impregnated catalysts are compared with the control, or portion of the Co-TiO$_2$ catalyst similarly treated except that no promoter metal was added thereto. The effectiveness of the metal added to the Co-TiO$_2$ catalyst, or metal promoter, is demonstrated by the amount of CO conversion obtained with each of the catalysts after the simulated regeneration.

EXAMPLE 1

Titania (Degussa P-25 TiO$_2$) was used as the support for preparation of several catalysts. The Degussa P-25 TiO$_2$ was admixed with Sterotex (a vegetable stearine used as a lubricant; a product of Capital City Products Co.) and, after pilling, grinding, screening to 80-150 mesh (Tyler), was calcined in air at 650° C. for 16 hours to give TiO$_2$ supports with the following properties:

| Rutile:Anatase Weight Ratio[1] | Surface Area m$^2$/g | Pore Volume ml/g |
| --- | --- | --- |
| 97:3 | 14 | 0.16 |

[1]ASTM D 3720-78.

A series of promoted 11% Co-TiO$_2$ catalysts was prepared by impregnation of the TiO$_2$ support using a rotary evaporator as described below, and these compared with an unpromoted 11% Co-TiO$_2$ catalyst in conducting a hydrocarbon synthesis operation.

The promoter metals were applied to the TiO$_2$ support simultaneously with the cobalt, the impregnating solvent used being acetone, acetone/15-20% H$_2$O, or water (Preparation A, B, or C), or by sequential impregnation from solution of a promoter metal, with intermediate air treatment at temperatures ranging from 140° C. to 500° C., with a final impregnation of the dried promoter-containing TiO$_2$ composite with a solution of cobaltous nitrate (Preparations D, E, F, G, and H). These catalyst preparation procedures are described below in Table I.

TABLE I

| Catalyst Preparation Procedures | |
| --- | --- |
| Simultaneous Impregnations | Solvent |
| A | Acetone |
| B | Acetone/15-20% H$_2$O |
| C | H$_2$O |

| Sequential Impregnations | Solvent for 1st Impregnation (Promoter) | Intermediate Air Treat Temperature °C. | Solvent for 2nd Impregnation (Cobalt Nitrate) |
| --- | --- | --- | --- |
| D | Isopropanol | 140 | Acetone |
| E | Acetone/15% H$_2$O | 140 | Acetone |
| F | Acetone/15% H$_2$O | 500 | Acetone |
| G | H$_2$O | 140 | Acetone |
| H | H$_2$O | 500 | H$_2$O |

Catalysts impregnated in this manner were dried in a vacuum oven at 140° C. for about 20 hours. Air treatments were made in forced-air ovens at various temperatures for 3 hours. The catalysts were diluted 1:1 by volume with 80-150 mesh TiO$_2$ (to minimize temperature gradients), charged to a ¼ inch ID reactor tube, reduced in H$_2$ at 450° C., 5000 V/Hr/V catalyst for one hour, and then reacted with syngas at 200° C., 280 psig, GHSV=1500 (on catalyst), and H$_2$/CO=2 for at least 16 hours. The performance of each catalyst was monitored by conventional GC analysis using neon as an internal standard (4% in the feed). Activity results are tabulated in Table II and shown in graphical form in FIGS. 1 and 2. High selectivity to heavy paraffinic hydrocarbons was obtained over all of these Co-TiO$_2$ catalysts independent of the promoters present. Thus, methane selectivity was about 3-5 mol. % and CO$_2$ selectivity was less than about 0.2 mol. % in all runs. The balance of the product was C$_2$+hydrocarbons.

TABLE II

Results of Catalyst Tests

| Promoter on 11% Co—TiO$_2$ | | | Prep. Procedure | Air Treat Temp. °C. 3 Hr. | % CO Conversion |
| --- | --- | --- | --- | --- | --- |
| Element | Compound | Wt. % | | | |
| None | — | — | A | — | 78 |
| " | | | " | 250 | 73 |
| " | | | " | 400 | 63 |
| " | | | " | 500 | 48 |
| " | | | " | 550 | 32 |
| " | | | " | 600 | 28 |
| Hf | HfO(NO$_3$)$_2$ | 0.06 | A | 500 | 48 |
| " | " | 0.31 | " | 400 | 78 |
| " | " | 0.31 | " | 500 | 73 |
| " | " | 0.50 | " | 500 | 70 |
| " | " | 0.50 | " | 600 | 58 |
| " | " | 0.63 | " | 500 | 71 |
| " | " | 1.89 | " | 500 | 78 |
| " | " | 3.0 | " | 500 | 81 |
| Ce | (NH$_4$)$_2$Ce(NO$_3$)$_6$ | 0.5 | B | — | 79 |
| " | " | 0.5 | B | 500 | 81 |
| " | " | 0.5 | E | 500 | 78 |
| " | " | 0.5 | F | 500 | 76 |
| " | " | 0.5 | B | 600 | 63 |
| " | " | 2.0 | B | 500 | 64 |
| " | " | 2.0 | H | 500 | 61 |
| Zr | Zr(OC$_3$H$_7$)$_4$ | 0.5 | D | — | 85 |
| " | " | 0.5 | D | 500 | 81 |
| " | ZrO(O$_2$CCH$_3$)$_2$ | 0.3 | G | — | 75 |
| " | " | 0.3 | C | — | 75 |
| " | " | 0.3 | C | 500 | 63 |
| " | " | 0.6 | C | 500 | 68 |
| " | " | 0.9 | C | — | 80 |
| " | " | 0.9 | C | 500 | 70 |
| " | " | 1.1 | C | 500 | 74 |
| U | UO$_2$(NO$_3$)$_2$ | 1.0 | A | 500 | 79 |

It is clear from these results, as depicted by reference to FIG. 1, that the zirconium, hafnium, cerium, or uranium promote, and maintain the activity of the 11% Co-TiO$_2$ catalyst after calcination. The activity of promoted 11% Co-TiO$_2$ thus remains high and virtually constant after calcination as high as 500° C. whereas, in contrast, the activity of the unpromoted 11% Co-TiO$_2$ catalyst declines rapidly, and sharply; the rate of activity decreasing dependent upon the temperature of calcination.

The data depicted in FIG. 2 clearly show the effectiveness of small amounts of zirconium, hafnium, cerium, and uranium to enhance the regenerability of a 11% Co-TiO$_2$ catalyst, promoters in concentration of about 0.5 wt. percent being adequate for near-maximum stabilization. Promoters in greater concentration do not appear to produce any significant additional benefit, if any.

The hydrocarbon product distribution was further defined in a run of an 11.2% Co-0.5% Hf-TiO$_2$ catalyst. The catalyst (150 cc) was diluted with 110 cc TiO$_2$, charged to a ½ inch ID reactor, reduced with H$_2$ at 450° C. for 4 hours, and then used for the conversion of syngas to hydrocarbons. Operating conditions and product distribution data are shown in Table III. The results confirm the formation of very heavy hydrocarbons over Co-Hf-TiO$_2$ catalyst.

TABLE III

Hydrocarbon Product Distribution From Co—Hf—TiO$_2$

| Temperature °C. | |
|---|---|
| Sandbath | 204 |
| Reactor Average | 206 |
| Gas Hourly Space Velocity on catalyst | 1000 |
| Pressure, psig | 280 |
| H$_2$/CO Inlet Ratio | 2.09 |
| % CO Conversion | 89 |
| Hydrocarbon Product Distribution, Wt. % | |
| C$_1$ | 5.6 |
| C$_2$-C$_4$ | 3.4 |
| C$_5$-550° F. | 15.1 |
| 550-700° F. | 10.0 |
| 700-1050° F. | 29.2 |
| 1050° F.+ | 36.7 |

The following example illustrates the catalysts of this invention used for the conversion of methanol to hydrocarbons.

EXAMPLE 2

Titania in the form of spherical beads was supplied by a catalyst manufacturer and employed to make catalysts. The titania was of 14–20 mesh size (Tyler), and characterized as having a rutile:anatase ratio of 86:14, a surface area of 17 m$^2$/g, and pore volume of 0.11 ml/gm. Catalysts were prepared from portions of the titania by simultaneous impregnation with aqueous solutions containing cobalt nitrate and a salt of ZrO(O$_2$CCH$_3$)$_2$, HfO(NO$_3$)$_2$, (NH$_4$)$_2$Ce(NO$_3$)$_6$ and UO$_2$(NO$_3$)$_2$, respectively. Each catalyst, after impregnation, was dried and air treated at 500° C. for three hours. The composition of each of these catalysts in terms of weight percent cobalt and weight percent concentration of the promoter (1 wt. %) is given in Table IV.

In separate runs, each of the promoted Co-TiO$_2$ catalysts were charged to a ⅜ inch ID reactor tube, reduced in hydrogen at 450° C., 1000 GHSV, and 0 psig for one hour. A feed admixture of hydrogen, argon, and methanol in molar ratio of 20 CH$_3$OH:1H$_2$:4Ar at CH$_3$OH LHSV=0.67, 230° C. and 400 psig was then passed over each of the catalysts. The performance of each catalyst was monitored by conventional GC analysis of the product with the results given in Table IV.

TABLE IV

CONVERSION OF METHANOL TO HYDROCARBONS
(230° C., 400 PSIG, LHSV = 0.67, 20 CH$_3$OH:1H$_2$:4 Ar)

| Catalyst Composition on TiO$_2$ | | | | | |
|---|---|---|---|---|---|
| Wt. % Co | 5.00 | 4.34 | 4.65 | 4.55 | 4.73 |
| Promoter (1 Wt. %) | None | Zr | Hf | Ce | U |
| % CH$_3$OH Conversion | 31 | 37 | 34 | 49 | 46 |
| Rate, g CH$_3$OH Converted/hr./g Co | 1.6 | 2.3 | 1.9 | 2.8 | 2.6 |
| Carbon Product Distribution, Wt. % | | | | | |
| CO | 16 | 13 | 16 | 10 | 9 |
| CO$_2$ | 8 | 9 | 7 | 9 | 13 |
| CH$_4$ | 8 | 8 | 8 | 7 | 9 |
| C$_2$+ | 68 | 70 | 69 | 74 | 69 |

The results show that the promoted catalysts are more active than unpromoted Co-TiO$_2$ catalysts, calcined at 500° C.; which is best shown by the methanol conversion rate. Cerium, as will be observed, is an especially good promoter for methanol conversion, the cerium promoted Co-TiO$_2$ catalyst giving the highest activity and best selectivity to C$_2$+hydrocarbons. The selectivity of the Co-TiO$_2$ catalyst generally by addition thereto of the respective promoter remains high, and to some extent improved by the presence of the promoter.

It is apparent that various modifications and changes can be made without departing the spirit and scope of the present invention.

What is claimed is:

1. A process useful for the conversion of methanol to hydrocarbons which comprises contacting said methanol at reaction conditions with a catalyst which comprises from about 2 percent to about 25 percent cobalt, based on the weight of the catalyst composition, composited with titania, or a titania-containing support, to which is added a zirconium, hafnium, cerium, or uranium promoter, the weight ratio of the zirconium, hafnium, cerium, or uranium metal:cobalt being greater than about 0.010:1; said reaction conditions being defined within ranges as follows:

Methanol:H$_2$ ratio: greater than about 4:1
Space Velocities, hr$^{-1}$: about 0.1 to 10
Temperatures, °C.: about 150 to 350
Methanol Partial Pressure, psia: about 100 to 1000.

2. The process of claim 1 wherein the weight ratio of the zirconium, hafnium, cerium, or uranium metal:cobalt ranges from about 0.04:1 to about 0.25:1.

3. The process of claim 1 wherein said promoter is hafnium.

4. The process of claim 1 wherein said promoter is zirconium.

5. The process of claim 1 wherein the catalyst contains from about 5 to about 15 percent cobalt, based on the weight of the catalyst compositions.

6. A process useful for the conversion of methanol to hydrocarbons which comprises contacting said methanol at reaction conditions with a catalyst which comprises cobalt in catalytically active amount composited with titania, or a titania-containing support, to which is added sufficient of a zirconium, hafnium, cerium, or uranium promoter to obtain, on conversion of methanol to hydrocarbons with deposition of coke on the catalyst, and the catalyst is regenerated by burning coke therefrom and then reactivated by contact with a reducing gas to reduce the cobalt, an activity, and activity maintenance at corresponding reaction conditions approximating that of a catalyst otherwise similar except that the cobalt-titania catalyst does not contain the added promoter, and has not been regenerated; said reaction conditions being defined within ranges as follows:

Methanol:$H_2$ ratio: greater than about 4:1
Space Velocities, $hr^{-1}$: about 0.1 to 10
Temperatures, °C.: about 150 to 350
Methanol Partial Pressure, psia: about 100 to 1000.

* * * * *